(12) United States Patent
Huggins et al.

(10) Patent No.: US 9,211,237 B2
(45) Date of Patent: *Dec. 15, 2015

(54) FILM FOAMING HYDROALCOHOLIC FOAM

(71) Applicant: STIEFEL RESEARCH AUSTRALIA PTY LTD, Rowville, Victoria (AU)

(72) Inventors: Joan Kathleen Huggins, Wheelers Hill (AU); Robert James Houlden, Kilsyth (AU)

(73) Assignee: STIEFEL RESEARCH AUSTRALIA PTY LTD, Rowville, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/028,981

(22) Filed: Sep. 17, 2013

(65) Prior Publication Data

US 2014/0017176 A1 Jan. 16, 2014

Related U.S. Application Data

(63) Continuation of application No. 11/187,217, filed on Jul. 22, 2005, now Pat. No. 8,562,959, which is a continuation of application No. PCT/AU2004/000170, filed on Feb. 12, 2004.

(60) Provisional application No. 60/447,445, filed on Feb. 12, 2003.

(51) Int. Cl.
| | |
|---|---|
| *A61K 8/04* | (2006.01) |
| *A61Q 17/04* | (2006.01) |
| *A61K 8/35* | (2006.01) |
| *A61K 8/37* | (2006.01) |
| *A61K 8/81* | (2006.01) |

(52) U.S. Cl.
CPC . *A61K 8/046* (2013.01); *A61K 8/35* (2013.01); *A61K 8/37* (2013.01); *A61K 8/8158* (2013.01); *A61Q 17/04* (2013.01)

(58) Field of Classification Search
CPC ........... A61K 8/046; A61K 8/35; A61K 8/37; A61K 8/8158; A61Q 17/04
USPC ......................................................... 424/43
See application file for complete search history.

(56) References Cited

U.S. PATENT DOCUMENTS

| | | | |
|---|---|---|---|
| 4,567,038 A | 1/1986 | Ciaudelli et al. | |
| 5,204,090 A | 4/1993 | Han | |
| 5,208,011 A | 5/1993 | Vaughan | |
| 5,985,294 A * | 11/1999 | Peffly | ............................ 424/401 |
| 6,113,888 A * | 9/2000 | Castro et al. | .................... 424/59 |
| 7,235,230 B2 | 6/2007 | LeGrow et al. | |
| 7,250,174 B2 | 7/2007 | Lee et al. | |
| 2002/0182234 A1 | 12/2002 | Riedel et al. | |
| 2006/0193789 A1 | 8/2006 | Tamarkin et al. | |

FOREIGN PATENT DOCUMENTS

| | | |
|---|---|---|
| CA | 2 068 061 C | 12/1992 |
| CA | 2 311 831 A1 | 12/2000 |
| CA | 2 444 533 C | 4/2002 |
| DE | 198 05 432 C1 | 3/1999 |
| GB | 1 557 580 A | 12/1979 |
| GB | 2 345 636 A | 7/2000 |
| JP | 63-230622 A | 9/1988 |
| JP | 08-119831 A | 5/1996 |
| JP | 11-505254 T | 5/1999 |
| JP | 2000516571 A | 12/2000 |
| JP | 2002534453 A | 10/2002 |
| JP | 2003011200 | 1/2003 |
| WO | 96/36322 A1 | 11/1996 |
| WO | 97/03559 A1 | 2/1997 |
| WO | 97/42933 A1 | 11/1997 |
| WO | 01/05366 A1 | 1/2001 |
| WO | 03/011238 A2 | 2/2003 |

OTHER PUBLICATIONS

Supplementary European Search Report, Application No. EP 04 71 0305, mailed Feb. 13, 2012, five (5) pages.

"Personal Care Polymers: Speciality Products from National Starch and Chemical Company", DERMACRYL Skin Care Formulating Guide, 1993, pp. 1-7, National Starch and Chemical Company, Bridgewater, New Jersey, USA.

Battistini, G., "Un moderno tensio—attivo non ionico", Rivista Italian Essenze, Profumi, Piante Officinali, Aromi, Saponi, Cosmetici, Aerosol, v. 98, n. 7, p. 422-427, 1966 (English summary of article appears on pp. 426-427).

Brazilian Office Action prepared Nov. 19, 2013, for counterpart Brazilian application PI0407373-8.

* cited by examiner

*Primary Examiner* — Janet Epps-Smith
*Assistant Examiner* — Courtney Brown
(74) *Attorney, Agent, or Firm* — Nath, Goldberg & Meyer; Joshua B. Goldberg; Tanya E. Harkins

(57) ABSTRACT

The present invention provides a foam composition comprising an active agent. In particular, the foam composition produces a water resistant, preferably very water resistant, film upon application.

14 Claims, No Drawings

FILM FOAMING HYDROALCOHOLIC FOAM

CROSS-REFERENCE TO RELATED APPLICATIONS

The present application is a Continuation Application of U.S. application Ser. No. 11/187,217 filed Jul. 22, 2005, which was a Continuation Application of PCT/AU04/00170 filed Feb. 12, 2004, and claims priority to U.S. Provisional Patent Application No. 60/447,445, filed Feb. 12, 2003, the disclosure of which hereby incorporated by reference in its entirety for all purposes.

BACKGROUND OF THE INVENTION

Topical delivery of active compounds is well known. Unfortunately, many topical delivery formulations are not waterproof or water resistant. Thus, when these active agents are applied to the skin and exposed to moisture, most of the active agents are often washed away from the skin thereby reducing their effectiveness.

There are many challenges in the topical application of active agents. For example, application of active agents should be easy and smooth. Moreover, in some instances the composition should remain within the applied area for a prolonged period even when exposed to moisture to provide a relatively constant amount of the active agent within the applied area.

Water resistant or very water resistant formulations of topical delivery systems are especially desirable because they eliminate the need for reapplication after exposure of the applied area to water, such as after swimming, bathing or excessive perspiration. This is particularly true for sunscreen products.

Sunscreen products provide protection for the human skin against damages of ultraviolet light. Products with various sun protection factor (SPF) values are available, thus allowing consumers to choose the amount of protection desired. While a variety of sunscreen products are available, "water resistant" or "very water resistant" sunscreens are especially desirable because they eliminate the need for reapplication after swimming, bathing or excessive perspiration. Generally "water resistant" sunscreen formulations can undergo at least about 40 minutes of water immersion without significant SPF loss, whereas "very water resistant" sunscreen formulations can undergo at least about 80 minutes of water immersion without significant SPF loss.

Ideally, sunscreen products should be stable and easy to apply, and provide acceptable consistency and skin-feel. The foregoing factors, which are important to achieving consistent distribution on the skin, even sun protection, along with consumer acceptance and commercial viability, are largely functions of the vehicle which carries the sunscreen agents.

For the above reasons, it is clearly desirable to formulate a topical vehicle that is capable of providing acceptable consistency, skin feel and stability, and is easy to use and apply sunscreen agents, and, thereby, achieve both water resistant character and high-SPF values. The present invention fulfills such needs.

SUMMARY OF THE INVENTION

The present invention provides a hydroalcoholic foam that comprises an active agent. Advantageously, the hydroalcoholic foam of the present invention is useful for topical application as it is easy to apply. As such, in one aspect, the present invention provides a composition in a pressurized container for forming a hydroalcoholic foam, wherein the composition comprises:
    at least one active agent;
    a water insoluble film-forming polymer;
    a hydroalcoholic foaming agent; and
    an aerosol propellant.

In one particular embodiment, the active agent is a sunscreen component. Preferably, the sunscreen component comprises at least one UVB sunscreen and/or at least one UVA sunscreen.

When applied to the skin, the water insoluble polymer forms a thin film of a water resistant, preferably very water resistant, barrier. In this manner, the active agent remains within the applied skin area even when wet.

In another aspect, the present invention provides a hydroalcoholic foaming agent which comprises a $C_1$-$C_6$ alcohol, water, wax and a surfactant. Preferably, the amount of water present in the composition is greater than the amount of $C_1$-$C_6$ alcohol.

These and other objects, embodiments and advantages will become more apparent with reference to the detailed description which follows.

DETAILED DESCRIPTION OF THE INVENTION

I. Definitions

Unless the context requires otherwise, the terms "active agent", "active compound" and "active component" are used interchangeably herein and refer to a substance having a cosmetic, pharmaceutical, pharmacological or therapeutic effect.

Unless indicated otherwise, a "water resistant" composition includes a "very water resistant" composition.

Unless otherwise indicated, all percentages recited herein are weight percentages, based upon total composition weight excluding the propellant.

Unless otherwise indicated "comprises"/"comprising" and grammatical variations thereof when used in this specification are to be taken to specify the presence of stated features, integers, steps or components or groups thereof, but do not preclude the presence or addition of one or more other features, integers, steps, components or groups thereof.

All disclosures referred to herein are hereby incorporated by reference.

II. General

The present invention provides various topical delivery foam compositions for active agents. In particular, compositions of the present invention are directed to water resistant, preferably very water resistant, topical delivery foam compositions comprising active agents. A water resistant property of the active agent is achieved by applying the foam composition to a desired topical area, e.g., skin, which then forms a thin film of a water resistant layer. The compositions of the present invention are contained in a pressurized container. When the composition is dispensed from the container, it forms a foam structure. The rubbing or shearing action of foam application breaks down the foam structure leaving behind a water resistant film of active agent.

In particular, the composition that is contained within the pressurized container comprises: at least one active agent; a water insoluble film-forming polymer; a hydroalcoholic foaming agent; and an aerosol propellant. The amount of each of these components can vary depending on a wide variety of factors, such as the desired foam characteristics, the degree of water resistance, and the like.

Typically, the pressurized container is any container that has a sufficient mechanical strength to withstand the pressure. The container is generally fitted with a valve, e.g., an upright or inverted valve, and a conventional foam spout actuator.

In addition, the present invention provides various aspects related to such compositions, including methods for protecting the skin of a subject from ultraviolet light and the use of the compositions in protecting skin against the negative effects of ultraviolet light.

In certain preferred embodiments, the compositions of the present invention are emulsions. In these instances, oil is preferably the dispersed liquid (the discontinuous phase) and the hydroalcoholic solution is the continuous phase. Typically oil in hydroalcoholic emulsions are difficult to stabilize. Therefore, one advantage of this invention is a stable hydroalcoholic film such as a hydroethanolic foam, and more preferably a stable hydroalcoholic film forming foam.

III. Active Agents

The active agent can be any cosmetic agent or pharmaceutically active agent, including sunscreen components, antibiotics, antifungal agents, antiviral compounds, nicotine, as well as other pharmaceutical or therapeutically active agents that are capable of being used topically. Exemplary antifungal agents that are suitable in compositions of the present invention include, but are not limited to, diols, allylamines (including naftifine and terbinafine), polyene macrolide antibiotics (including amphotericin and nystatin), triazole derivatives (such as fluconazole), fatty acids (such as caprylic and propionic acid), amorolfine, ciclopirox, lamine, benzoic acid, flucytosine, haloprogin, tolnaftate, undecenoic acid and its salts, griseofulvin and imidazole compounds (such as ketoconazole and chlorphenesin (3-(4-Chlorphenoxy)propane-1, 2-diol)).

The terms "antibiotic" and "antimicrobial" are used herein interchangeably to refer to a compound that inhibits the growth of, inhibits the virulence of, or kills bacterial cells. Antibiotics include, e.g., substances produced by various species of microorganisms (e.g., bacteria, fungi, and actinomycetes), variants thereof, and synthetic antibacterial agents. A complete list of antibiotics is too long to be included herein, and those of skill in the art are aware of the multitude of antibiotics that can be used in the present invention. See, e.g., Chambers and Sande, *Antimicrobial Agents: General Considerations* in Goodman & Gilman's The Pharmacological Basis of Therapeutics, Hardman and Limbard eds., (1996); and Kucers, et al., *The Use of Antibiotics: A Clinical Review of Antibacterial, Antifungal, and Antiviral Drugs* Oxford Univ. Press (1997). Suitable antibiotic agents include, but are not limited to, clindamycin, erythromycin, tetracycline, minocycline, doxycycline, penicillin, ampicillin, carbenicillin, methicillin, cephalosporins, vancomycin, and bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, inezolid, pharmaceutically acceptable salts thereof, and prodrugs thereof. Preferably, the antibiotic agent is clindamycin, erythromycin, tetracycline, minocycline, doxycycline, pharmaceutically acceptable salts thereof, or prodrugs thereof.

In certain preferred aspects, the active agent is a light sensitive drug such as an antibiotic (e.g., amikacin, augmentin amoxicillin, ampicillin, cefazolin, cefoxitin, ceftazidime, ceftiofur, cephalothin, enrofloxacin, florfenicol, gentamicin, imipenem, kanamycin, sarafloxicin, tetracycline, ticarcillin, and tilmicosin) an antifungal or other light sensitive pharmaceutical actives such as tretinoin, isotretinoin, sodium sulfacetamide, calcipotriene and hydroquinone. Those of skill in the art will know of other light sensitive active agents suitable for use in the present invention.

Other suitable pharmaceutical agents are well known to one skilled in the art. See, for example, The Merck Index, 13$^{th}$ Ed., 2001, Merck & Co., Inc., Whitehouse Station, N.J., pp. THER-1 to THER-31, which is incorporated herein by reference in its entirety. The compositions of the present invention can comprise a mixture of two or more cosmetic agents and/or pharmaceutically active agents. In this manner, a wide combination of active agents can be used simultaneously. For example, the active agent can be a mixture of a sunscreen component and a light sensitive pharmaceutical agent, e.g., an antibiotic compound. The sunscreen component protects the light sensitive pharmaceutical agent from sun light. Moreover, the water resistant property allows the subject to pursue active outdoor activities, e.g., swimming and other physical activities, which can cause perspiration, without having the active agent being washed away.

In one particular embodiment of the present invention, the active agent is a sunscreen component. The term "sunscreen component" as used herein includes commonly used ultraviolet ray-blocking compounds. Preferably, the sunscreen component comprises at least one UVB sunscreen and/or at least one UVA sunscreen. More preferably, the sunscreen component comprises at least one UVB sunscreen and at least one UVA sunscreen. As expected, the combination of UVB and UVA sunscreens provide a broad spectrum UV protection. A more detailed discussion of sunscreen agents useful in this invention is provided by Roelandts et al., "A Survey of Ultraviolet Absorbers in Commercially Available Sun Products", Int. J. Dermatol., Vol. 22, pp. 247-255 (May, 1983).

In another embodiment, the sunscreen component is preferably selected from the group of: Aminobenzoic acid (4-Aminobenzoic acid); Avobenzone (4-tert-butyl-4-methoxydibenzoylmethane); Benzophenone-2 (Bis(2,4-Dihydroxyphenyl)Methanone); Benzophenone-3 (Oxybenzone); Benzophenone-4 (Sulisobenzone); Benzophenone-5 (Sulisobenzone sodium); Benzophenone-8 (Dioxybenzone); Benzylidene Camphor (3-(4-Methylbenzylidene)-d-1camphor); Cinoxate; Ecamsule (Terephthalylidene dicamphor sulfonic acid); Ethoxylated ethyl 4-aminobenzoic acid (PEG25 PABA); Homosalate (Homomethyl salicylate); Isoamylmethoxycinnamate (Isopentenyl-4-methoxycinnamate); Isopropylbenzyl salicylate; Menthyl anthranilate (Methyl 2-aminobenzoate); Mexoryl XL (phenol,2-(2H-benzotriazol-2-yl)-4-methyl-6[2-methyl-3-[1,3,3,3-tetramethyl-1-[(trimethylsilyl)oxy]disiloxanyl]propyl)Octyl dimethyl PABA; Octinoxate (Octyl methoxycinnamate); Octyl salicylate (2-Ethylhexyl Salicylate); Octocrylene (2-cyano-3,3-diphenyl acrylic acid,2-ethyl hexyl ester); Octyl triazone (2,4, 6-Trianalino-(p-Carbo-2'-ethylhexyl-1'oxy)1,3,5-Triazine); Padimate O (2-Ethylhexyl 4-dimethylaminobenzoate); Phenylbenzimidazole sulfonic acid (2-Phenylbenzimidazole-5-sulfonic acid) and its potassium, sodium and triethanolamine salts; N,N,N-Trimethyl-4-(oxoborn-3-ylidenemethyl) anilinium methylsulfate; Salicylic acid salts (potassium,sodium and triethanolamine); Tinosorb M. (2,2'-Methylenebis-6-(2H-benzotriazol-2yl)-4-(tetramethyl-butyl)-1,1,3,3-phenol); Titanium dioxide; Triethanolamine salicylate; Zinc oxide; and mixtures thereof.

The nature and the amount of sunscreen component present in the composition generally affects the sun protection factor (SPF) of the composition. Thus, a wide SPF range, is possible in compositions of the present invention. Typically, however, the amount of a particular sunscreen used is determined by the desired SPF. As such, SPF as low as two (2) and as high as 45 or greater can be achieved by adjusting the amount of sunscreen present in the composition. Generally, however, sunscreens having SPF of about 15 or about 30 are most commonly used. However, it should be appreciated that the sunscreen compositions of the present invention are not limited to any particular SPF values.

The sunscreen component can also be used as an agent to protect light sensitive drugs. Therefore, in one embodiment, the present invention provides a combination of a light sensitive active agent and a sunscreen active agent.

As stated above, the amount of sunscreen component present in compositions of the present invention vary depending on the particular sunscreen component(s) chosen and the SPF desired. Typically, however, compositions of the present invention comprise from about 1 to about 30% by weight of the total composition in the container, including the propellant. Preferably, the amount of sunscreen component present in compositions of the present invention is from about 5 to about 40% Alternatively, at least about 5%, preferably at least about 10%, of the sunscreen component is present in compositions of the present invention. The amount of sunscreen referred to herein refers to the total amount of all sunscreen components that are present in compositions of the present invention. As such, for a composition comprising a mixture of sunscreen components, the amount of each sunscreen component can vary significantly depending on the desired physical and chemical properties as well as the SPF desired.

IV. Water Insoluble Film-Forming Polymer

Typically, the water insoluble film-forming polymer is preferably a carboxylated acrylic copolymer. Water insoluble carboxylated acrylic copolymers including those sold by National Starch and Chemical Corporation under the trade names "Dermacryl", "Amphomer" and "Versacryl" (acrylates/octylacrylamide copolymer) (CFTA), are known to be useful in this invention. Particularly preferred carboxylated acrylic copolymer is a solid copolymer sold under the trade name "Dermacryl-79," which provides satisfactory water resistant and/or very water resistant properties. In addition, "Amphomer," or "octylacrylamide/acrylate/butylaminoethyl methacrylate copolymer," a polymer formed from octylacrylamide, t-butylaminoethyl methacrylate and two or more monomers of acrylic acid, methacrylic acid or any of their simple esters, can also be employed. Dermacryl 79 CAS Number 129702-02-9 is a hydrophobic, high molecular weight carboxylated acrylic copolymer.

Advantageously, the carboxylic acid functional groups of the film-forming polymers are at least partially neutralized in order to obtain good dispersion of the film-forming polymer in the aqueous medium. In certain aspects, a percentage of the carboxylic acid groups present in the water insoluble carboxylated acrylic copolymer are neutralized. Preferably, the percentage that is neutralized is between 0% to about 40%. Preferably, the percentage that is neutralized is between about 3% to about 35%, more preferably about 7% to about 33%, and most preferably about 10% to about 30%, such as 10%, 11%, 12%, 13%, 14%, 15%, 16%, 17%, 18%, 19%, 20%, 21%, 22%, 23%, 24%, 25%, 26%, 27%, 28%, 29% and 30%.

The carboxylic acid functional groups can be neutralized using a basic compound, such as an inorganic base, such as sodium hydroxide, sodium benzoate or potassium hydroxide, or an amino-alcohol selected for example from 2-amino-2-methyl-1-propanol (AMP), triethanolamine, triisopropanolamine (TIPA), monoethanolamine, diethanolamine, tris[2-hydroxy-1-propyl]amine, 2-amino-2-methyl-1,3-propanediol (AMPD), alkaline salts of ethylene diamine tetra acetic acid such as tetrasodium ethylene diamine tetra acetic acid ($Na_4EDTA$), or 2-amino-2-hydroxymethyl-1,3-propanediol. Lysine, arginine or cystine can also be used as neutralizing agents, or combinations of the foregoing. Preferably, the carboxylated acrylic copolymer is neutralized using sodium benzoate and/or tetrasodium EDTA.

Generally, compositions of the present invention have about 0.01 to about 15 weight percent of a carboxylated acrylic copolymer. The range is preferably from about 0.1% to about 10%, with about 0.5% to about 5% being especially preferred.

It is known that these polymers become water dispersible/soluble via neutralization of their carboxyl (i.e., carboxylic acid) groups with a base, e.g., an alkaline material. Thus, in some embodiments of the present invention, a portion of the carboxyl groups in the carboxylated acrylic copolymer is neutralized with a base. In this manner, the amount of organic solvent, e.g., $C_1$-$C_6$ alcohol, used in the composition can be reduced significantly.

V. Hydroalcoholic Foaming Agent

The hydroalcoholic foaming agent comprises a $C_1$-$C_6$ alcohol, water, wax and a surfactant.

A. Alcohols

Suitable $C_1$-$C_6$ alcohols include methanol, ethanol, propanol, butanol, pentanol, hexanol and their isomers. However, since methanol is poisonous, for safety reasons ethanol n-propanol or isopropanol are preferred. With ethanol being particularly preferred, such as "SD Alcohol 40" or "SDA 40".

In one particular embodiment, the amount of water in the hydroalcoholic foaming agent is higher than the amount of alcoholic solvent, e.g., $C_1$-$C_6$ alcohol. Preferably, the amount of $C_1$-$C_6$ alcohol present in the composition is less than about 50% by weight of the total composition, more preferably less than about 40% and most preferably, less than about 30%. Alternatively, the amount of $C_1$-$C_6$ alcohol present in the composition of the present invention ranges from about 5% to about 40% by weight, preferably from about 10% to about 30% and more preferably from about 15% to about 25%, such as 16%, 17%, 18%, 19%, 20%, 21%, 22%, 23%, 24%, and fractions thereof.

B. Water

Typically at least about 40% of the composition is comprised of water, preferably at least about 45% and more preferably at least about 50%. Alternatively, the amount of water present in the compositions of the present invention generally ranges from about 35 to about 65%, preferably from about 40 to about 60% and more preferably from about 50 to about 55%. Thus, unlike other conventional water resistant compositions, compositions of the present invention have a significantly higher amount of water than the amount of $C_1$-$C_6$ alcohol.

C. Wax

Various waxes are suitable for use in the present invention. These include for example, non-ionic self-emulsifying waxes. For example, Polawax GP200 (cetearyl alcohol and PEG-20 stearate) (Croda Surfactants) is a non-ionic self-emulsifying wax that is used in oil-in-water emulsions. The waxy material was used to impart structural support to the foam and to improve the film-forming properties and water resistance of the emulsion on the skin. Other waxes suitable for use in the present invention include, but are not limited to, natural waxes such as animal waxes such as carnauba and bees wax, vegetable waxes, mineral waxes such as petroleum waxes, and synthetic waxes.

D. Surfactants

Compositions of the present invention can also include a surfactant system. The presence of surfactant allows emulsification of one or more components that may be otherwise insoluble within the composition. The surfactant system of the invention can comprise a polyoxyalkylene ester of a straight or branched chain fatty acid, polysorbate or mixtures thereof. Preferred polyoxyalkylenes include polypropylene glycol and polyethylene glycol, with the latter being especially preferred.

Useful polyoxyalkylene esters of fatty acid include, but are not limited to, the fatty acid esters of polyoxyethylene glycol sold as a "Cithrol" (Croda) and "Myrj 52" (Uniqema). Useful polysorbate includes Polysorbate 85 sold as "Crillet 45" (Croda). The surfactant system can also include combinations of one or more surfactants disclosed herein.

Generally, the total amount of surfactant(s) present in compositions of the present invention ranges from about 0.1 to about 20% by weight. The preferred range is from about 0.5% to about 15%, with about 2% to about 10% being highly preferred.

VI. Optional Components

The compositions of the invention can also include suitable amounts of cosmetically and pharmaceutically acceptable additives, i.e., excipients and/or chemically active adjuvants, including chelating agents, such as EDTA and its salts, and corrosion protecting agents, such as sodium benzoate, or preservatives.

In addition, other additives such as colorants, thickeners, perfumes, fillers, diluents, carriers, plasticizers, stabilizers, gelling agents, preservatives, supplemental emollients/solvents and the like can also be added.

VII. Use

When dispensed from the container, the compositions of the present invention form a foam structure. When the foam is applied to a desired area, it dries relatively quickly to leave a water resistant or very water resistant active agent film on the skin.

The melting point of the hydroalcoholic foam that is produced from compositions of the present invention is about 35° C. or higher. Preferably, the foam melting temperature is about 40° C. or higher. An especially preferred foam melting temperature is about 45° C. or higher. The term "foam melting temperature" refers to the temperature at which the foam structure breaks down without any application of force, e.g., rubbing.

Additional objects, advantages, and novel features of this invention will become apparent to those skilled in the art upon examination of the following examples thereof, which are not intended to be limiting.

VIII. Examples

1. Example 1

This example illustrates various preferred components to formulate a stable sunscreen foam for use on the scalp, face and body.

a) Sunscreen Component

Parsol MCX (octinoxate) is a highly effective, oil soluble UV-B absorber with maximum absorption at 308 nm. In addition, Parsol MCX is an excellent solvent for Uvinul M40. A concentration of 7.5% w/w was chosen based on the monograph requirements.

Uvinul M40 (oxybenzone) is an oil soluble UV-A and UV-B absorber offering maximum absorption in the shortwave UV-B and UV-A spectra. Uvinul M40 is usually employed as a coabsorber in combination with a specific UV-B absorber (such as Parsol MCX). Uvinul M40 requires sufficient solubility in emulsions to ensure that re-crystallization does not occur.

Parsol 1789 (butyl methoxydibenzolymethane) is a highly effective oil-soluble UV-A filter. It is often used in conjunction with UV-B filters to provide full-spectrum UV protection. The maximum absorption of Parsol 1789 is at or near 360 nm.

b) Excipients

Polawax GP200 (cetearyl alcohol and PEG-20 stearate) (Croda Surfactants) is a non-ionic self-emulsifying wax that is used in oil-in-water emulsions. The waxy material was used to impart structural support to the foam and to improve the film-forming properties and water resistance of the emulsion on the skin.

Dermacryl® 79 (acrylates/octylacrylamide copolymer) (National Starch & Chemical) is a hydrophobic, high molecular weight, polymer. It was used at a level of about 1.5-2.5% w/w in the formulation. It forms a water resistant or water proof film when applied. Its highly water resistant property was used to produce a water resistant sunscreen product.

Myrj 52 (PEG-40 Stearate) (Uniqema) is a non-ionic emulsifier that was used in conjunction with Crillet 45 to obtain a desired HLB (hydrophobic lipophilic balance) system for the formulation. Myrj 52 is preferred to other emulsifiers because it is a solid waxy material. A concentration of 1.5-2.5% was used based on a HLB screening (using different ratios of Myrj 52 and Crillet 45), and as a result of foam quality optimization.

Crillet 45 (Polysorbate 85) (Croda Surfactants) is an oil-in-water emulsifier. It was used at a concentration of 0.5-1.2% in association with Myrj 52 to achieve a desired HLB.

Sodium Benzoate is a commonly used corrosion inhibitor and about 0.10-0.30% was added to the system to prevent can corrosion during storage.

Disodium EDTA (BASF) is a chelating agent that was added to the system at 0.05-0.20%. It is known to one skilled in the art that Parsol 1789 reacts with metals, particularly $Fe^{+2}$, during manufacture or storage and develops a red complex that discolors the formulation.

The sunscreen foam formulation is a non-greasy, water resistant, SPF 15 foam product that can be used on the head, face and body. One particular sunscreen component formulation is shown below.

Parsol MCX—7.5% w/w (in the absence of propellant)
Uvinul M40—4.0% w/w (in the absence of propellant)
Parsol 1789—2.0% w/w (in the absence of propellant)

The foam melting temperature of the formulation was found to be about 40° C.

c) Water Resistance

Dermacryl requires neutralization and heating to be incorporated into standard creams. In one embodiment, the present invention utilizes a new manufacturing method, whereby dissolving the Dermacryl in the ethanol first, then combining this with the warm oil phase (40-45° C.) before forming the emulsion has the advantage of not having to heat the ethanol, thus providing a safer method of manufacture than traditional techniques where a hot oil/ethanol phase is added to a hot water phase.

The acrylic copolymer with carboxyl groups such as Dermacryl 79, is insoluble in water, thereby imparting wash resistance in a formulation. If the carboxyl groups are fully neutralized, the acrylic copolymer would be water soluble, hence impart no wash resistance. A partially neutralized copolymer (for example, 29% neutralization), has been surprising found to show enhanced water solubility over an un-neutralised formulation, and improved wash resistance over a fully neutralized formulation. An example of a fully (100%) neutralized formula is given below: An example of a fully (100%) neutralized formula is given below in Table 1:

TABLE 1

| Item No. | Ingredient | % w/w |
|---|---|---|
| 1 | Purified Water | 52.11 |
| 2 | Sodium Benzoate | 0.19 |
| 3 | EDTA di-Sodium | 0.10 |
| 4 | Polawax GP200 | 2.85 |
| 5 | Parsol MCX | 7.13 |
| 6 | Uvinul M40 | 3.80 |
| 7 | Parsol 1789 | 1.90 |
| 8 | Crillet 45 | 0.83 |
| 9 | Ethomeen C25 | 3.92 |
| 10 | Dermacryl-79 | 1.90 |
| 11 | Ethanol SDA 40-2 | 20.27 |
|  | TOTAL | 95.00 | plus propellant at 5% w/w.

The effect of partially neutralized and fully neutralized Dermacryl-79 in the formulation was investigated. SPF results of the formulations are shown below: 100% neutralized Dermacryl 79—SPF 3.9 (40-minutes wash resistance) Table 1. 29% neutralized Dermacryl 79—SPF 16.1 (40-minutes wash resistance) (Table 3).

d) Neutralization of Dermacryl

Dermacryl 79 is carboxylated and is normally neutralized with a suitable alkaline material in formulation. The formulator can use materials such as triethanolamine, 2-amino-2-methyl-1-propanol, ammonium or potassium hydroxides, or long chain amines. The amount of base required to neutralize the carboxyl groups in DERMACRYL 79 can be determined by the following relationship:

$$B = \frac{W \times 2.4 \times N \times E}{1000}$$

Where: B=weight (grams) of base needed; W=weight (grams) of DERMACRYL 79 used; N=% neutralization required (decimal); and E=equivalent weight of base (eq/g). A specific example of 100% neutralization of 100 grams of DERMACRYL 79 with triethanolamine is as follows: EXAMPLE: W=100 grams; N=1.00; E=149.2;

$$B = \frac{100 \times 2.4 \times 1.00 \times 149.2}{1000} = 35.8 \text{ grams TEA.}$$

Tables 2 and 3 show different SPF 15 foam compositions of the present invention. The partially neutralized formula is set forth below (Table 3).

TABLE 2

| SPF 15 Foam | | |
|---|---|---|
| Trade Name | % w/w (No propellant) | % w/w (with propellant) |
| Ethanol SDA 40-2 | 24.96 | 23.71 |
| Dermacryl 79 | 2.00 | 1.90 |
| Polawax GP200 | 3.00 | 2.85 |
| Parsol MCX | 7.50 | 7.13 |
| Uvinul M40 | 4.00 | 3.80 |
| Parsol 1789 | 2.00 | 1.90 |
| Myrj 52 | 1.20 | 1.14 |
| Purified Water | 54.24 | 51.53 |
| Sodium Benzoate | 0.20 | 0.19 |
| di-sodium EDTA | 0.10 | 0.095 |
| Crillet 1 | 0.80 | 0.76 |
| Propellant P70 | 0 | 5.00 |

TABLE 3

| SPF 15 Foam | | | |
|---|---|---|---|
| Trade Name | % w/w (No propellent) | % w/w (with propellant) | Function |
| Deionized Water | 56.30 | 53.49 | Solvent |
| Alcohol SDA 40-2 | 21.90 | 20.81 | Solvent |
| Parsol MCX | 7.50 | 7.13 | Sunscreen-UVB |
| Propellant P45 | 0.00 | 5.00 | Propellant |
| Uvinul M-40 | 4.00 | 3.80 | Sunscreen-UVA |
| Polawax GP200 | 3.00 | 2.85 | Emulsifier |
| Myrj 52 | 2.13 | 2.02 | Emollient |
| Parsol 1789 | 2.00 | 1.90 | Sunscreen-UVA |
| Dermacryl-79 | 2.00 | 1.90 | Film Former |
| Crillet 45 | 0.87 | 0.83 | Emulsifier |
| Sodium Benzoate | 0.20 | 0.19 | Anti-corrosion protection |
| di-sodium EDTA | 0.10 | 0.10 | Chelating agent |

2. Example 2

This example illustrates a method of manufacturing the compositions of the present invention.

The sunscreen formulations of the present invention can be produced using the following procedure. The particle size and emulsion appearance were assessed using an Olympus BX50 microscope. The ambient manufacturing method of manufacture is set out below:

a) Water Phase:
1. Weigh purified water into a vessel. Heat to 45-50° C.
2. While stirring add Myrj 52, continue to stir until the Myrj 52 has dissolved.
3. While stirring, add Sodium Benzoate, stir until dissolved.
4. While continuing to stir the product, add bisodium EDTA, stir until dissolved.
5. Stir cool to 20-30° C.
6. Correct for any loss of water.

b) Ethanol Phase:
7. Weigh Ethanol into a separate tank.
8. While stirring, slowly add Dermacryl 79, continue to stir until dissolved.

Oil Phase:
9. Weigh Parsol MCX into a separate vessel and heat to 50-55° C.
10. While stirring, add Crillet 45, Uvinul M40, Parsol 1789 and Polawax GP200, continue to stir until all components have dissolved.
11. Stir cool to 40-45° C.
12. While stirring, slowly add the oil phase to the ethanol phase and continue to stir until dissolved.

13. Correct for any loss of Ethanol.
14. Maintain at 20-30° C.
c) Emulsion Formation:
15. While stirring the water phase, slowly add the Ethanol/Oil phase into the vortex.
16. Homogenise batch until the particle size is within specification.
17. Slow stir to allow the batch to de-aerate.

3. Example 3

This example shows percent neutralization can have an effect on water resistance.

The results indicate that at 0% neutralization and at 25% neutralization of the Dermacryl, the water resistance of the film was higher than the 100% neutralized film. While the partial neutralization of the Dermacryl allowed it to be solubilised in the formulation, the formulation still provided good water resistance. From this, it can further be expected that the partially neutralized Dermacryl formulation would provide better SPF than the 100% neutralized Dermacryl formulation post immersion in water.

TABLE 4

|  | Product: | | | | | |
| --- | --- | --- | --- | --- | --- | --- |
|  | Sunscreen Foam F210/04/05 E210/04/05 30% EtOH 25% Neutralization | | Sunscreen Foam F210/04/13 E210/04/13 10% Ethanol 0% Neutralization | | Sunscreen Foam F210/04/18 E210/04/18 10% Ethanol 100% Neutralization | |
|  | 1 | 2 | 1 | 2 | 1 | 2 |
| Wt of microscope slide (T): | 16.8371 | 17.2195 | 16.7635 | 16.7936 | 17.5840 | 17.1021 |
| Wt of microscope slide plus product: | 18.1036 | 18.3680 | 17.7508 | 17.8898 | 18.6974 | 18.1176 |
| *Wt of product applied to microscope slide: | 1.2665 | 1.1485 | 0.9873 | 1.0962 | 1.1134 | 1.0155 |
| After 15 hrs at 25° C./5 mins at ambient | 17.0993 | 17.4681 | 16.9861 | 17.0297 | 17.8473 | 17.3413 |
| After 60 mins at 50° C./5 mins at ambient | 17.0953 | 17.4641 | 16.9861 | 17.0264 | 17.8445 | 17.3392 |
| After 135 mins at 50° C./5 mins at ambient | 17.0939 | — | — | 17.0258 | 17.8442 | 17.3390 |
| After 180 mins at 50° C./5 mins at ambient | — | 17.4628 | 16.9860 | — | — | — |
| After 210 mins at 50° C./5 mins at ambient | — | — | — | — | — | — |
| ⟨MF1⟩ | 17.0939 | 17.4628 | 16.9860 | 17.0258 | 17.8442 | 17.3390 |
| Immerse in static waterbath at 25° C. for 20 mins | | | | | | |
| 60 mins at 50° C./5 mins at ambient | — | 17.4000 | | | | |
| 90 mins at 50° C./5 mins at ambient | 17.0281 | | | | | |
| 140 mins at 50° C./5 mins at ambient | 17.0169 | | | | | |
| 170 mins at 50° C./5 mins at ambient | 17.0119 | | | | | |
| After 62 hrs at 25° C./5 mins at ambient | 16.9976 | | | | | |
| 120 mins at 50° C./5 mins at ambient | 16.9964 | | | | | |
| ⟨MF2⟩ | 16.9964 | 17.3833 | 16.9201 | 16.9461 | 17.6531 | 17.1623 |
| Washability (in water) - % Weight Loss | 62 | 67 | 70 | 66 | 27 | 25 |
| AVERAGE WATER RESISTANCE | 65 | | 68 | | 26 | |

As shown below in Table 4, 0% and 25% neutralization show exceptional water resistance capabilities.

The in vitro water resistance testing involves applying an accurately weighed mass of sunscreen foam formulation to an accurately weighed substrate (ie glass microscope slide). The product is placed in an incubator and allowed to dry to a film.

The substrate with the dried film is placed into a waterbath with shaking, after which it is returned to an incubator and redried.

The water resistance of each film is calculated as the percentage of film remaining on the substrate.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A composition in a pressurized container for forming a hydroalcoholic foam, said composition comprising:
   a sunscreen component;
   a water insoluble film-forming polymer which is a water insoluble carboxylated acrylic copolymer;
   a hydroalcoholic foaming agent comprising a C1-C6 alcohol present in an amount from about 5% to about 40% by weight based on the total weight of the composition, water, wax and surfactant; and
   an aerosol propellant;
   and wherein said composition forms a foam when released from the container, and said foam, in use, forms a water resistant film on skin, and
   wherein a percentage of the carboxylic acid groups that are present in the water insoluble carboxylated acrylic copolymer are neutralized and the percentage neutralization is between about 3% to about 35%.

2. The composition of claim 1, wherein said sunscreen component comprises at least one UVB sunscreen and/or at least one UVA sunscreen.

3. The composition of claim 2, wherein said sunscreen component is selected from the group consisting of Aminobenzoic acid (4-Aminobenzoic acid); Avobenzone (4-tert-butyl-4-methoxydibenzoylmethane); Benzophenone-2 (Bis(2,4-Dihydroxyphenyl) Methanone); Benzophenone-3 (Oxybenzone); Benzophenone-4 (Sulisobenzone); Benzophenone-5 (Sulisobenzone sodium); Benzophenone-8 (Dioxybenzone); Benzylidene Camphor (3-(4-Methylbenzylidene)-d-1 camphor); Cinoxate; Ecamsule (Terephthalylidene dicamphor sulfonic acid); Ethoxylated ethyl 4-aminobenzoic acid (PEG25 PABA); Homosalate (Homomethyl salicylate); Isoamylmethoxycinnamate (Isopentenyl-4-methoxycinnamate); Isopropylbenzyl salicylate; Menthyl anthranilate (Methyl 2-aminobenzoate); Mexoryl XL (phenol,2-(2H-benzotriazol-2-yl)-4-methyl-6[2-methyl-3-[1,3,3,3-tetramethyl-1-[(trimethylsilyl)oxy]disiloxanyl]propyl); Octyl dimethyl PABA; Octinoxate (Octyl methoxycinnamate); Octyl salicylate (2-Ethylhexyl Salicylate); Octocrylene (2-cyano-3,3-diphenyl acrylic acid, 2-ethyl hexyl ester); Octyl triazone (2,4,6-Trianalino-(p-Carbo-2-ethylhexyl-1'oxy) 1,3,5-Triazine); Padimate O (2-Ethylhexyl 4-dimethylaminobenzoate); Phenylbenzimidazole sulfonic acid (2-Phenylbenzimidazole-5-sulfonic acid) and its potassium, sodium and triethanolamine salts; N,N,N-Trimethyl-4-(oxoborn-3-ylidenemethyl) anilinium methylsulfate; Salicylic acid salts (potassium, sodium and triethanolamine); Tinosorb M (2,2'-Methylene-bis-6-(2H-benzotriazol-2yl)-4-(tetramethyl-butyl)-1,1,3,3-phenol); Titanium dioxide; Triethanolamine salicylate; Zinc oxide; and a mixture thereof.

4. The composition of claim 3, wherein said sunscreen component is selected from the group consisting of octinoxate, oxybenzone, avobenzone, and a mixture thereof.

5. The composition of claim 1, wherein the total amount of said sunscreen component is from about 1% to about 30% by weight based on the total weight of the composition.

6. The composition of claim 1, wherein said water insoluble carboxylated acrylic copolymer is selected from the group consisting of acrylate/t-octylpropenamide, octylacrylamide/acrylate/butylaminoethyl methacrylate copolymer, acrylates/octylacrylamide copolymer, and a mixture thereof.

7. The composition of claim 6, wherein said water insoluble carboxylated acrylic copolymer is acrylates/octylacrylamide copolymer.

8. The composition of claim 1, wherein said percentage neutralization is between about 7% to about 33%.

9. The composition of claim 1, wherein said carboxylated acrylic copolymer is neutralized using sodium benzoate.

10. The composition of claim 1, wherein the total amount of said carboxylated acrylic copolymer is about 0.1% to about 10% by weight based on the total weight of the composition.

11. The composition of claim 1, wherein the amount of said C1-C6 alcohol is from about 10% to about 30% by weight based on the total weight of the composition.

12. The composition of claim 1, further comprising a chelating agent.

13. The composition of claim 2, further comprising a corrosion protection agent.

14. The composition of claim 1, wherein said foam, in use, forms a very water resistant film on the skin.

* * * * *